United States Patent
Prasad et al.

(10) Patent No.: US 6,200,136 B1
(45) Date of Patent: Mar. 13, 2001

(54) FIBER-REINFORCED DENTAL BRIDGE AND METHOD OF MANUFACTURE THEREOF

(75) Inventors: Arun Prasad, Cheshire; Ajit Karmaker, Wallingford; Elie Zammarieh, Milford, all of CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/130,581

(22) Filed: Aug. 7, 1998

(51) Int. Cl.$^7$ ....................................................... A61C 5/00
(52) U.S. Cl. ............................................. 433/180; 433/215
(58) Field of Search .................................. 433/180, 215, 433/181, 182, 183, 226

(56) References Cited

U.S. PATENT DOCUMENTS

| | | |
|---|---|---|
| 726,381 | 4/1903 | Von Unruh . |
| 1,324,331 | 12/1919 | Garcia De La Beldad . |
| 1,382,830 | 6/1921 | Hagaman . |
| 1,483,781 | 2/1924 | Churchill . |
| 2,152,069 | 3/1939 | Lifschutz . |
| 2,672,686 | 3/1954 | Herzberg . |
| 4,231,740 | 11/1980 | Shoher et al. . |
| 4,269,595 | 5/1981 | Nemethy . |
| 4,457,714 | 7/1984 | Klein . |
| 4,758,162 | 7/1988 | Dobbs . |
| 4,764,116 | 8/1988 | Shoher et al. . |
| 4,798,536 | 1/1989 | Katz . |
| 4,826,436 | 5/1989 | Shoher et al. . |
| 4,867,683 | * 9/1989 | Meisel ................................... 433/180 |
| 4,877,400 | 10/1989 | Holsclaw . |
| 4,950,162 | * 8/1990 | Korber et al. ........................ 433/180 |
| 5,000,687 | 3/1991 | Yarovesky et al. . |
| 5,074,791 | 12/1991 | Shoher et al. . |
| 5,098,304 | 3/1992 | Scharf . |
| 5,281,563 | 1/1994 | Komma et al. . |
| 5,308,391 | 5/1994 | Komma et al. . |
| 5,346,866 | 9/1994 | Komma et al. . |
| 5,552,350 | 9/1996 | Hornor . |
| 5,653,791 | 8/1997 | Panzera et al. . |
| 5,816,816 | * 10/1998 | Scharf ................................... 433/215 |
| 5,921,778 | * 7/1999 | Karmaker et al. .................... 433/215 |

FOREIGN PATENT DOCUMENTS

| | | | |
|---|---|---|---|
| 6237948 | * 8/1994 | (JP) ...................................... 433/215 |
| 9408783 | * 4/1994 | (WO) .................................... 433/180 |

OTHER PUBLICATIONS

Nixon, Robert, The Advent of Metal–Free Dentistry: A Versatile New Fiber and Polymer–Glass System, Supp Practical Periodontics and Aesthetic Dentistry, Oct. 1997.*

* cited by examiner

Primary Examiner—Ralph A. Lewis
(74) Attorney, Agent, or Firm—Cantor Colburn LLP

(57) ABSTRACT

The present invention relates to unique dental structures such as bridges and crowns. The bridge comprises a structural component such as a fiber reinforced polymeric base material impregnated bar disposed within interproximal cavities located in the distal occlusal surface of the mesial abutment tooth and the mesial occlusal surface of the distal abutment tooth, and a support element of woven fibers and polymeric base material. The support element can span the endentulous area, wrap around the structural component, and provide support for the veneer on the pontic.

13 Claims, 3 Drawing Sheets

FIBER-REINFORCED DENTAL BRIDGE AND METHOD OF MANUFACTURE THEREOF

BACKGROUND OF THE INVENTION

1. Field of the Invention

The present invention relates to dental restoration devices and methods of manufacture thereof. In particular, this invention relates to dental bridges comprising at least one fiber-reinforced structural component and a method of manufacture thereof.

2. Brief Description of the Related Art

In the dental arts, a bridge is a device for the restoration and replacement of one or more natural teeth. It replaces at least one missing tooth and is supported on either side by the remaining teeth. A bridge generally comprises a pontic for replacement of the missing tooth, and connectors which connects the pontic to a retaining member such as a crown formed on an abutment tooth adjacent the pontic. By their nature, bridges must be aesthetic, as well as strong, in order to withstand forces generated by mastication of various types of foods and to maintain the positions of the abutting teeth. Prior art bridges therefore often incorporate a structural reinforcing element to provide strength, and a veneer to provide aesthetics, including ceramic or particulate-filled resin composite veneers.

Not surprisingly, construction of such dental bridge is often a time consuming, involved, and complex process requiring multiple steps. Accordingly, a number of bridge designs are disclosed in the prior art which are intended to either enhance strength or ease of preparation. For example, U.S. Pat. No. 5,074,791 discloses a bridge comprising a preformed pontic, which simplifies preparation. The so-called winged bridge disclosed in U.S. Pat. No. 5,000,687 is designed to enhance bridge strength. U.S. Pat. No. 4,877,400 to Holsclaw discloses a dental bridge comprising a metal pontic rod that is opaqued and installed in refractory model notches. The metal ponltic rod and abutment teeth are coated with a porcelain mix and cured. Since metal is opaque to visible light, metal bridges fail to offer optimum aesthetic qualities. U.S. Pat. No. 4,758,162 to Dobbs discloses a dental bridge comprising a wax occlusal bar and at least one removable wax pontic.

A prefabricated dental bridge in U.S. Pat. No. 4,764,116 to Schoher et al. discloses a prefabricated pontic having a framework that is adjustable by use of a plurality of pliable metal members which interconnect for an open skeleton framework. U.S. Pat. No. 4,457,714 to Klein discloses a prefabricated dental bridge comprising a vertically-orientated pontic element and a pair of horizontally-extending bars disposed on opposite sides of the pontic element.

One problem experienced in prior art bridges featuring particulate-filled resin composite veneers is fracture of the veneer under tensile loading, due to a low strain-to-failure values of the composites. Veneers that are unsupported (due to poor framework design) are also vulnerable to shear under occlusal/incisal loading. Thus, while suitable for their intended purposes, there still remains a need for dental bridges which are aesthetically pleasing, strong and simple for the dentist or dental technician to prepare, and which possess sufficient structural integrity to withstand the stresses associated with mastication.

SUMMARY OF THE INVENTION

The above-discussed and other problems and deficiencies of the prior art are overcome or alleviated by the bridge support element and method of preparation therefor, of the present invention, comprising: a structural component having fibers embedded within a first polymeric base material, said structural component disposed across the edentulous area and supported by the abutment teeth; and a support element having woven fibers embedded within second polymeric base material compatible with said first polymeric base material, said support member disposed in and having a size and geometry so as to fit in the edentulous area below said structural component.

The process for dental restoration of the present invention, comprises the steps of: disposing a support element fibers embedded within polymeric base material and a size and geometry to fit within an edentulous area between a mesial abutment tooth and a distal abutment tooth in said edentulous area; disposing a structural component capable of spanning said edentulous area in interproximal cavities in the mesial and distal abutment teeth over said support element; and curing said support element and structural components.

The above-discussed and other features and advantages of the present invention will be appreciated and understood by those skilled in the art from the following detailed description and drawings.

BRIEF DESCRIPTION OF THE DRAWINGS

For the purpose of illustrating the invention, there are shown in the drawing forms which are presently preferred; it being understood that this invention is not limited to the precise arrangements and instrumentalities shown. Referring now to the drawings wherein like elements are numbered alike in the several FIGURES.

DESCRIPTION OF THE PREFERRED EMBODIMENT

Figure 1:
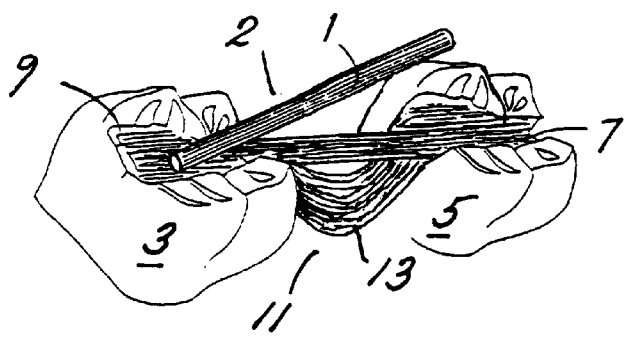
FIGS. 1, 2, 3, and 4, are views in section of a bridge having a hammock-shaped support element in accordance with embodiments of the present invention both with (1 and 2), and without (3), structural reinforcement of the occlusal surface.

The present invention is directed to a bridge for replacing one or more missing natural teeth, wherein the bridge comprises firstly a reinforcing structural component which spans the abutment teeth, and secondly a support element which supports a sculpting composite. Both the reinforcing structural component and the support element comprise reinforcing fibers and a polymerizable resin, or base material. In dental restoration, critical factors effecting the selection of materials for utilization include: biocompatability and lack of toxicity; with factors such as structural integrity, diametral tensile strength, water sorption, index of refraction, shrinkage, aesthetics, and the ability to withstand mastification stresses also being important. The various materials employed are altered for a particular use by varying physical characteristics, i.e. opacity, hue, chroma, value, rheology (viscosity) and bonding properties, the use of, type, and amount of reinforcing materials and/or fillers, and the degree of cure employed at various stages of the restoration.

The base material, otherwise commonly referred to as the polymeric matrix after polymerization, is selected from those known in the art of dental materials, including, but not limited to, polyamides, polyesters, polyolefins, polyimides, polyarylates, polyurethanes, vinyl esters or epoxy-based materials, styrenes, styrene acrylonitriles, ABS polymers, polysutfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. Preferred base materials include those based on acrylic, methacrylic and vinyl monomers, for example those disclosed in U.S. Pat. Nos. 3,066,112, 3,179,623, and 3,194,784 to Bowen;

U.S. Pat. Nos. 3,751,399 and 3,926,906 to Lee et al.; and commonly assigned U.S. Pat. Nos. 5,276,068 to Waknine (hereby incorporated by reference). An especially preferred methacrylate monomer is the condensation product of bisphenol A and glycidyl methacrylate, 2,2'-bis[4-(3-methacryloxy-2-hydroxy propoxy)-phenyl]-propane (hereinafter abbreviated BIS-GMA), the condensation product of ethoxylated bisphenol A and glycidyl methacrylate (hereinafter abbreviated EBPA-DMA), and the condensation product of 2 parts hydroxymethylmethacrylate and 1 part triethylene glycol bis-(chloroformate) (hereinafter abbreviated PCDMA).

The base material may further comprise a co-polymerizable diluent monomer which is generally used to adjust the viscosity of the polymerizable composition to affect wettability of the composition. Suitable diluent monomers include, without limitation, hydroxyalkyl methacrylates, such as 2-hydroxyethylmethacrylate, 1,6-hexanedioldimethacrylate, and 2-hydroxypropylmethacrylate; glyceryl dimethacrylate; ethyleneglycolmethacrylates, including ethyleneglycolmethacrylate, diethyleneglycolmethacrylate, triethyleneglycolmethacrylate and tetraethyleneglycolmethacrylates, and diisocyanates, such as 1,6-hexamethylene diisocyanate, with triethyleneglycoldimethacrylate (TEGDMA) particularly preferred for use in the present invention due to its low viscosity and high cross-linking capability.

The base material, which typically includes polymerization initiators, and accelerators, ultra-violet light absorbers, anti-oxidants, fluorescent whitening agents, free radical initiators, and/or other additives well known in the art, may be photo-curable, self-curing, dual curing, or vacuum, heat, or pressure curable compositions, as well as any combination thereof. Heat curable compositions which are typically polymerized under controlled atmosphere and include a heat cure initiator such as benzoyl peroxide, 1,1'-azobis (cyclohexanecarbonitrile) or other free radical initiator. The preferred base material is both light and heat curable, wherein light effects partial cure of the base material, while final curing is by heat under controlled atmosphere. Preferred methacrylate-based dual-cure materials are available from JENERIC/PENTRON, Inc., Wallingford, Conn., under the trademarks SCULPTURE® and FLOW-IT®.

The base material may further comprise particulate fillers known in the art. Suitable fillers include those capable of being covalently bonded to the base material itself or to a coupling agent that is covalently bonded to the base material and the filler. Fillers include silica, silicate glass, quartz, barium sulfate, barium silicate, strontium silicate, barium borosilicate, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include A-174 (γ-methacrylate propyl tri-methoxy silane), produced by OSI Specialties, NY.

Possible reinforcing fibers, which are preferably used in accordance with U.S. Pat. Nos. 4,717,341 and 4,894,012 to Goldberg et al. (hereby incorporated by reference), include glass, carbon, graphite, polyaramid, and mixtures thereof, as well as other fibers known in the art. These fibers can be in the form of unidirectional, continuous filaments, weaves, random, nonwoven, mesh, or otherwise oriented fibers, and of random or uniform length.

In order to enhance the bond between the reinforcing fibers and base material, thereby enhancing the reinforcing effect, the fibers may be silanized or otherwise treated, for example, etched, chemically grafted, plasma treated, and/or ion-bombarded, as well as others. Etching, which roughens the fiber surface to enhance bonding, employs an acid, such as hydrofluoric acid, 1.23% acidulated phosphate fluoride, or others. Silanation renders the fibers hydrophobic, thereby reducing water sorption, improving hydrolytic stability of the fiber reinforced base material, as well as improving wetting and mixing, and thus contributing to better mechanical properties. Silanation comprises treating the fibers with vinyl-tris(β-methoxyethoxy)silane,-methacryloxypropyltrimethoxysilane, β-(3,4-epoxycyclohexyl)-ethyltrimethoxysilane, γglycidoxypropyltrimethoxysilane, γ-aminopropyltriethoxysilane, N-β-(aminoethyl)-γ-aminopropyltrimethoxysilane and/or other commercially available coupling agents commonly utilized in the dental arts.

The reinforcing structural component may include up to about 10 wt % of one or more particulate fillers, with the specific amount of such filler(s) being determined by whether the structural component will be disposed within or supported by the support element. Although woven, random, mesh or otherwise oriented fibers of uniform or random length can be employed in the reinforcing structural component, a bar shape having a suitable dimension is preferred for use in the structural component with unidirectional, continuous fibers having a length substantially equivalent to the length of the structural component especially preferred due to the enhanced strength obtained under flexural bonding. The structural component preferably comprises at least about 20 weight percent (wt %) and preferably about 20 wt % to about 70 wt % fibers.

Although the reinforcing structural component may be formed from the fibers and base material by the dentist or technician and then shaped into the required structural component, the fibers are preferably intimately mixed with the base material, for example by compression molding or pultrusion, and either provided to the dentist or technician in this form for ultimate shaping or formed into the ultimate shape and provided to the dentist or technician for use. The geometry of the structural component may be rectangular, rhomboidal, ovoidal, cylindrical, or of any other cross-sectional configuration effective to provide strength, stiffness, and structural integrity to the finished bridge.

The support element, which improves the overall strength of the final bridge, reducing shear fracture under occlusal/incisal loading, and which particularly supports the sculpturing material, comprises fibers preferably impregnated with base material, and can contain up to about 50 wt % particulate filler, with about 5 to about 50 wt % particulate filler preferred (relative to base material). The fibers can be in the form of unidirectional fibers, a woven fabric or a random arrangement, with a woven fabric or mesh preferred because of both increased strength provided by fibers being in different orientations, and for ease of construction.

The sculpting material, conventionally also referred to as veneer, comprises up to about 95 wt % particulate filler dispersed in base material. Preferably the sculpting material comprises between about 50 wt % and about 90 wt % particulate filler, with about 70 wt % to about 85 wt % particulate filler substantially homogeneously dispersed in the base material especially preferred. Although any base material can be used, a base material compatible with the support element, structural component, and the filler used in the sculpturing material is preferred. The base material used in the reinforcing structural component, the support element, and the veneer may be the same or different, so long as the materials are compatible.

Formation of the bridge using the structural component and support element comprises: preparation of the abutment teeth; formation of the reinforcing structural component and support element in relation to the abutment teeth, edentulous area, and interproximal cavities; adaptation of the support element and structural component (free hand or under the influence of a force); and formation of a pontic to form and contour using sculpturing material.

For example, the abutment teeth are prepared similarly to typical shoulder preparations for full coverage bridges, i.e. with a 90°–100° cavosurface angle with approximately 1.0millimeter (mm) axial reduction and 1.5 mm occlusal reduction. After conventional preparation of the abutment teeth, interproximal cavities such as small (2 mm×2 mm×2 mm) boxes, are cut into abutment teeth, providing a space to rest the structural component. While interproximal boxes are preferred, rest platform(s) or ledges formed from sculpting material or indentations or cavities of any geometry capable of holding the structural component in place may be used, with the size of the interproximal cavities dictated by the size of the structural component and other considerations such as the age of the teeth. (Younger teeth with a large pulp chamber will require preparation of a smaller box.) A channel of about 1×1 mm on the occlusal floor may be used for resting the structural component.

Following preparation of the abutment teeth with interproximal cavities, conventional methods can be used to form a negative impression of the abutment teeth including the interproximal cavities and the edentulous area. A positive model or die is then formed from the negative impression and utilized to form the structural component.

Where interproximal boxes are used, a thin layer (about 0.3 to about 0.5 mm) of sculpting material compatible with the structural component and support element is preferably applied to the trimmed, prepared die, and optionally cured prior to the application of the support element and/or reinforcing structural component. Such layer prevents exposure of the reinforcing structural component of support element to the natural teeth. A thin veneer of sculpting material is also placed at the bottom of the die to form the gingival floor anatomy. The ends of the support elements may extend completely over the occlusal floor.

The longest distance above the edentulous area, between the two facing walls (mesial and distal) of the prepared interproximal cavities, is measured and the structural component is fabricated. The structural component should have a length, width, and height sufficient to span the measured distance, remain supported in the interproximal cavities, and impart the desired structural integrity to the pontic, enabling it to withstand the stresses associated with mastication. The structural component may be provided to the dentist or technician as a prefabricated composite or it may be fabricated by the dentist or technician. In a particularly preferred embodiment, the structural component is supplied to the dentist or technician in the form of a strips with the fibers pre-impregnated with uncured base material. This form is easy for the dentist or technician to manipulate and form into the required shapes since the base material retains a degree of malleability.

Typically, forming a structural component of these strips comprises cutting several pieces of strips of the required length. Sufficient cuttings are then preferably pressed together, via rolling or other appropriate means, so as to attain the desired size and geometry structural component, to reduce the number of voids, and to place the individual strips in intimate contact. It is especially preferred to remove substantially all voids between the strips, i.e. greater than 85%, to improve structural integrity.

The support element is also prepared based upon the size of the edentulous area. As is shown in the Figures, the support element can be a single or multiple layers or plies of pre-impregnated fibers, and can have a shape to substantially span the endentulous area from abutment tooth to abutment tooth and from the occlusal surface to the gingival floor. Preferably the support element is substantially hammock shaped or otherwise having a larger cross-sectional geometry toward the center with a substantially smaller cross-sectional geometry toward the ends, similar to a crimped tubular structure (refer to the Figures).

Figure 2:
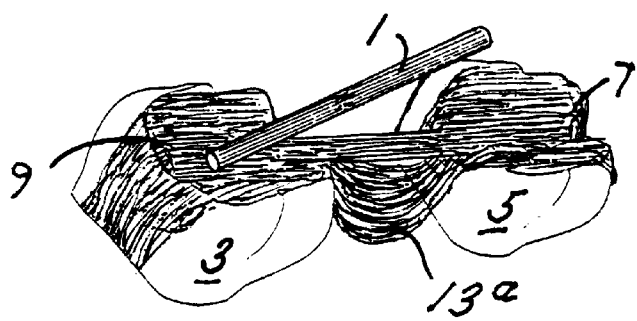

Various embodiments of the bridge are provided in FIGS. 1–8. In FIG. 1 reinforcing structural component 1 is shown spanning occlusal area 2, supported in interproximal cavities 7, 9 of abutment teeth 3, 5. Support element 13 is shown spanning edentulous area 11 below structural component 1, supporting the sculpturing material (not shown) surrounding the structural component 1 and forming the pontic (not shown). Meanwhile, FIG. 2 shows a support element 13$^a$ similar to FIG. 1, but where the support element 13$^a$ substantially covers the occlusal surface of abutment teeth 3,5, and can even cover one or more sides thereof down to the gum line.

Figure 3:
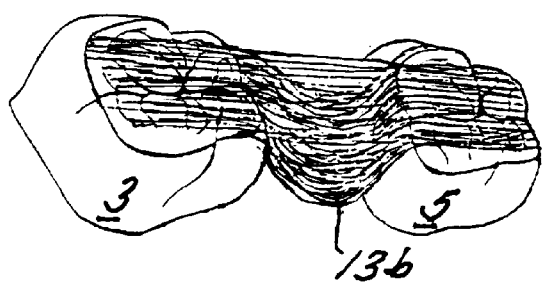

FIG. 3 shows another support element 13$^b$ located within the edentulous area and attached to the occlusal surfaces of the abutment teeth 3, 5. This support element 13$^b$, which is shown in a cut-out, exploded view in FIG. 5, comprises a woven fiber embedded within base material 20, with additional fiber reinforced layers 21, 22, 23. One or both of these additional fiber reinforced layers 21, 22, 23 comprises woven, non-woven, mesh, randoom, or unidirectional reinforcing fibers embedded in a base material compatible with the woven fiber layer 20.

Figure 4:
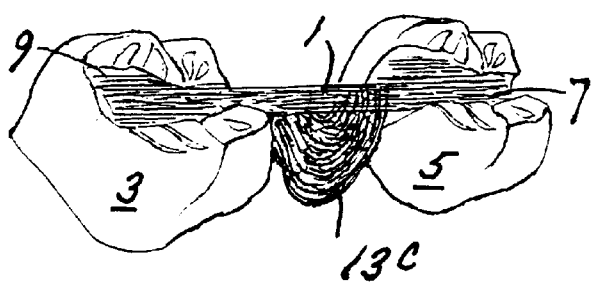
Figure 5:
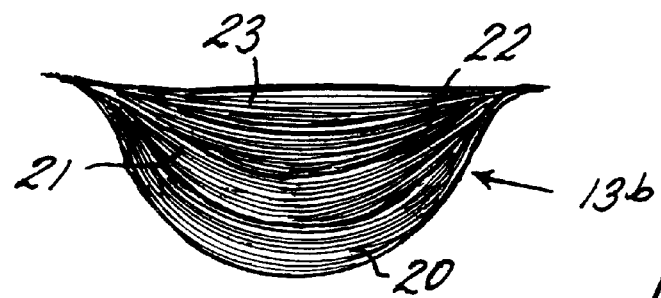
FIG. 5 is a view in section of a hammock-shaped support element in accordance with another embodiment of the present invention, having stacked fiber/resin layers.

FIG. 4 shows a support element 13$^c$ used in conjunction with and attached to structural component 1. Where structural component 1 spans the endentulus area and is supported in cavities 7, 9, while the support element 13$^c$ is solely supported by the structural component 1.

Figure 6:
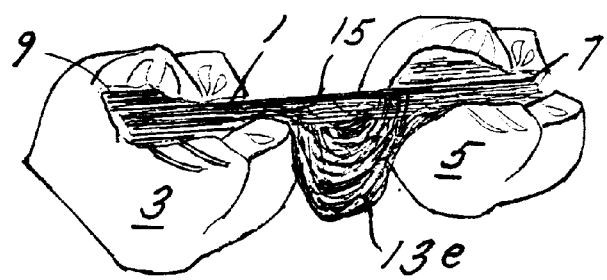
FIG. 6 is a schematic drawing of a further embodiment of the present invention having a hammock shaped support element, occlusal surface support, and wrap support.
Figure 7:
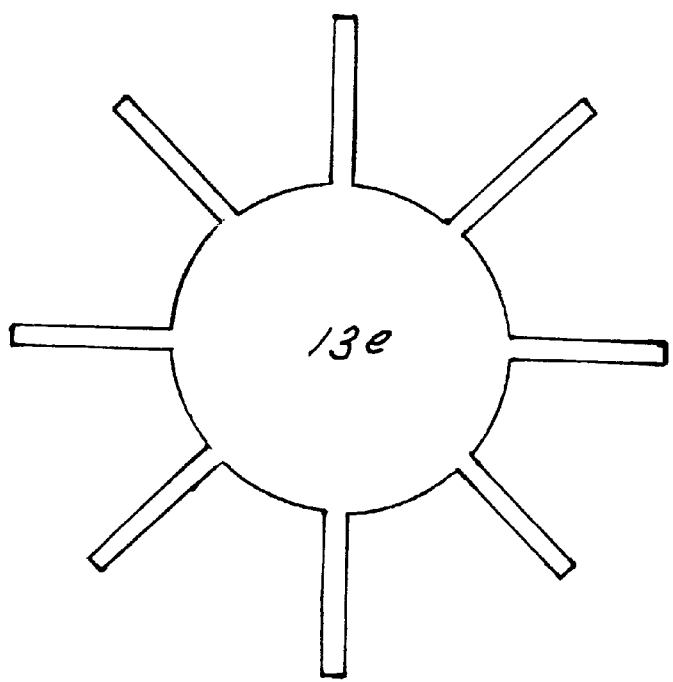
FIG. 7 is a top view of one embodiment of a support element/wrap combination component of the present invention.

FIG. 6 is another embodiment of the support element 13$^e$ used in conjunction with the structural component 1 and wrap 15. The wrap 15 can comprise ribbon as described above in relation to the structural component, and/or reinforcing fibers embedded within base material as described in relation to the support element above. In this embodiment, the wrap 15 intimately contacts and secures the structural component 1 to the support element 13$^E$. The wrapping can be accomplished via the use of separate components or via the design shown in FIG. 7 where the wrap and support element are one component.

Figure 8:
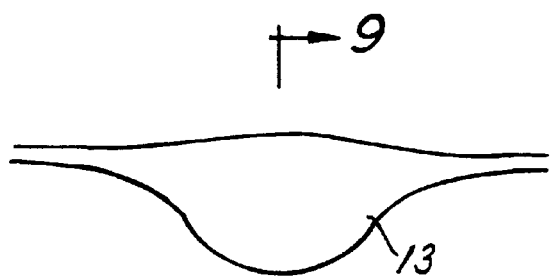
FIG. 8 is a schematic drawing of another embodiment of a support of the present invention including an occlusal surface support disposed within a support element.
Figure 9:
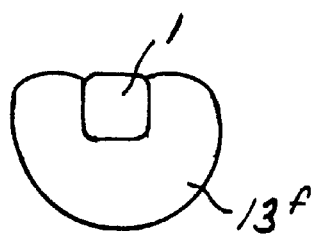
FIG. 9 is a cross-sectional view of an embodiment of the support element shown in FIG. 8 showing the occlusal surface support disposed within the support element.
Figure 10:
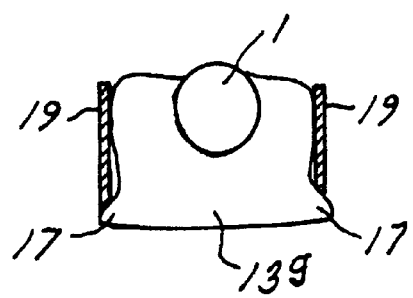
FIG. 10 is a cross-sectional view of another embodiment of the support element shown in FIG. 8 showing a support element having a ledge.

FIG. 8, a cross-sectional views of which are shown in FIGS. 9 and 10, shows a support element 13 enclosing and intimately contacting structural component 1. FIG. 9 shows the structural component 1 cocooned within the support element 13$^f$, while FIG. 10 additionally shows supports 17 for providing additional structural integrity to the sculpting material 19.

A pontic may then be placed or built up around the structural component and support element usinig methods known in the art.

The dental restoration, including the structural component, support element, and pontic which is formed from sculpting material, may be prepared within the patient's mouth or from the dies described above. Either preparation can employ techniques and substances, such as clamps, the use of partial curing to stiffen the structural component and/or support element, or tacky resin to hold these in place.

Advantages of the present invention range from cost effectiveness and improved structural integrity due to reduced amount of sculpturing material required, improved tensile strain in the sculpting material due to the support element, and prevent shearing of the sculpting material via proper stress distribution to increased longevity of the bridge.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A dental restoration for replacing at least one missing tooth located in an edentulous area between a mesial abutment tooth and a distal abutment tooth, comprising:
    a structural component having fibers embedded within a first polymeric base material, said structural component disposed across the edentulous area and extending beyond said edentulous are for support by at least a portion of the occlusal area of the abutment teeth; and
    a support element having woven fibers embedded within second polymeric base material compatible with said first polymeric base material, said support element disposed in and having a size and geometry so as to fit in the edentulous area below said structural component and substantially extending from said structural component to the gingival floor.

2. A dental restoration as in claim 1, further comprising a pontic formed on said support element and said structural component, said pontic comprising sculpturing material disposed in the occlusal surface.

3. A dental restoration as in claim 1, wherein said support element has a larger cross-sectional geometry toward a center of said support element than a cross-sectional area near an end of said support element.

4. A dental restoration for replacing at least one missing tooth located in an edentulous area between a mesial abutment tooth and a distal abutment tooth, comprising:
    a support element having woven fibers embedded within a first polymeric base material, said support element disposed in and having a size and geometry so as to fit in the edentulous area and substantially extending from said structural component to the gingival floor; and
    a structural component having non-woven fibers embedded within a second polymeric base material compatible with said first polymeric base material, said structural component disposed across the edentulous area and extending beyond said edentulous area for sunport by at least a portion of the occlusal area of the abutment teeth, wherein said structural component is disposed within said support element.

5. A dental restoration as in claim 4, further comprising a pontic formed on said support element and said structural component, said pontic comprising sculpturing material disposed in the occlusal surface.

6. A process for dental restoration, comprising:
    disposing a support element having fibers embedded within polymeric base material and having a size and geometry of a hammock, with one side of said hammock capable of contacting the mesial interproximal cavity and another side of said hammock capable of contacting the distal interproximal cavity, to fit within an edentulous area between a mesial abutment tooth and a distal abutment tooth in said edentulous area;
    disposing a structural component capable of spanning said edentulous area in interproximal cavities in the mesial and distal abutment teeth over said support element; and
    curing said support element and structural component.

7. A process for dental restoration as in claim 6, wherein one or more support layers having fibers embedded within a polymeric base material are disposed between said support element and said structural component.

8. A process for dental restoration as in claim 7, wherein said fibers are woven, unilateral, or randomly distributed.

9. A process for dental restoration as in claim 6, further comprising wrapping at least one support layer around said support element and said structural component, said support layer having fibers disposed within a polymeric base material.

10. A process for dental restoration as in claim 6, wherein said structural component contacts said support element on at least three sides.

11. A process for dental restoration as in claim 6, further comprising coating at least a portion of said support element with sculpturing material.

12. A process for dental restoration, comprising:
    disposing a support element having fibers embedded within polymeric base material and having a size and geometry to fit within an edentulous area between a mesial abutment tooth and a distal abutment tooth in said edentulous area;
    disposing a structural component capable of spanning said edentulous area in interproximal cavities in the mesial and distal abutment teeth over said support element;
    coating at least a portion of said support with sculpting material, wherein said support element has at least one ledge for providing structural integrity to said sculpting material, said ledge protruding from said support element in a direction substantially perpendicular to the line between the mesial abutment tooth and the distal abutment tooth; and curing said support element and structural component.

13. A process for forming a dental restoration for replacing at least one missing natural tooth, using at least two abutment teeth each having an occlusal portion, comprising:

forming opposing first and second interproximal cavities in the distal occlusal portion of the mesial abutment tooth and in the mesial occlusal portion of the distal abutment tooth, respectively;

preparing at least one structural component comprising reinforcing fiber embedded within a polymeric matrix, said component having a sufficient size and geometry to span in and between said first interproximal cavity and said second interproximal cavity; and preparing a support element comprising a second fiber embedded with a resin;

attaching one end of said support element to one of said abutment teeth;

attaching another end of said support element to another of said abutment teeth; and disposing the structural component in and between the first and second interproximal cavities.

* * * * *

UNITED STATES PATENT AND TRADEMARK OFFICE
CERTIFICATE OF CORRECTION

PATENT NO.    : 6,200,136 B1
DATED         : March 13, 2001
INVENTOR(S)   : Prasad et al.

It is certified that error appears in the above-identified patent and that said Letters Patent is hereby corrected as shown below:

<u>Title page,</u>
Item [57], ABSTRACT,
Line 9, before "area" delete "endentulous" and insert therefor -- edentulous --

<u>Column 1,</u>
Line 15, before "the" delete "connects" and insert therefor -- connect --
Line 38, after "metal" delete "ponltic" and insert therefor -- pontic --
Line 55, after "to" delete "a"

<u>Column 2,</u>
Line 8, after "support" delete "member" and insert therefor -- element --

<u>Column 6,</u>
Line 19, after "of" delete "a"
Line 36, after "the" delete "endentulous" and insert therefor -- edentulous --
Line 65, delete "layer" insert therefor -- of base material --

<u>Column 7,</u>
Line 1, after "the" delete "endentulus" and insert therefor -- edentulous --
Line 53, after "edentulous" delete "are" and insert therefor -- area --

Signed and Sealed this

Twenty-sixth Day of October, 2004

JON W. DUDAS
*Director of the United States Patent and Trademark Office*